United States Patent [19]

Vial

[11] 3,990,444
[45] Nov. 9, 1976

[54] BLOOD TRANSFUSION APPARATUS
[75] Inventor: Guy Aimé Vial, Pont-de-Claix, France
[73] Assignee: Vial S.A.R.L., Eybens, France
[22] Filed: Nov. 25, 1974
[21] Appl. No.: 526,955

Related U.S. Application Data
[63] Continuation-in-part of Ser. No. 418,209, Nov. 21, 1973, abandoned.

[30] Foreign Application Priority Data
Nov. 22, 1972 France .............................. 72.42317

[52] U.S. Cl. ..................... 128/214 F; 128/DIG. 12; 222/63; 417/43; 417/477
[51] Int. Cl.² ..................... A61M 5/00; F04B 43/08
[58] Field of Search ........ 128/214 R, 214 C, 214 E, 128/214 F, 214 Z, DIG. 12, DIG. 13; 222/59, 63; 417/43, 477

[56] References Cited
UNITED STATES PATENTS
| 1,988,337 | 1/1935 | Santiago et al. | 417/477 |
| 2,434,802 | 1/1948 | Jacobs | 417/477 X |
| 2,483,924 | 10/1949 | Moulinier | 417/477 X |
| 3,163,176 | 12/1964 | Darling | 128/214 E |
| 3,366,071 | 1/1968 | Dutler | 417/477 |
| 3,425,415 | 2/1969 | Gordon et al. | 128/214 E |
| 3,736,930 | 6/1973 | Georgi | 128/214 E |
| 3,812,482 | 5/1974 | Clark | 128/214 E |

Primary Examiner—Dalton L. Truluck
Attorney, Agent, or Firm—Brisebois & Kruger

[57] ABSTRACT

This invention relates to a device adapted to be attached to a conventional transfusion tube of a blood-transfusion apparatus, said device permitting the drop-by-drop regulation and control of the flow-rate and comprising a mechanical pump comprising a plurality of rollers rotatably mounted around the periphery of a disc rotatably mounted within a casing chamber, said chamber having the same diameter as the envelope defined by said rollers, said casing having an opening therein and comprising a slidable member in said opening adapted to be biased by resilient means against said rollers, thus permitting the interposition between said slidable member and said rollers of transfusion tubes of different diameters. An air-bubble detector is provided which stops the pump if an air bubble is present in the transfusion tube, and the failure of any electrical or mechanical member actuates an optical and acoustic alarm signal.

5 Claims, 5 Drawing Figures

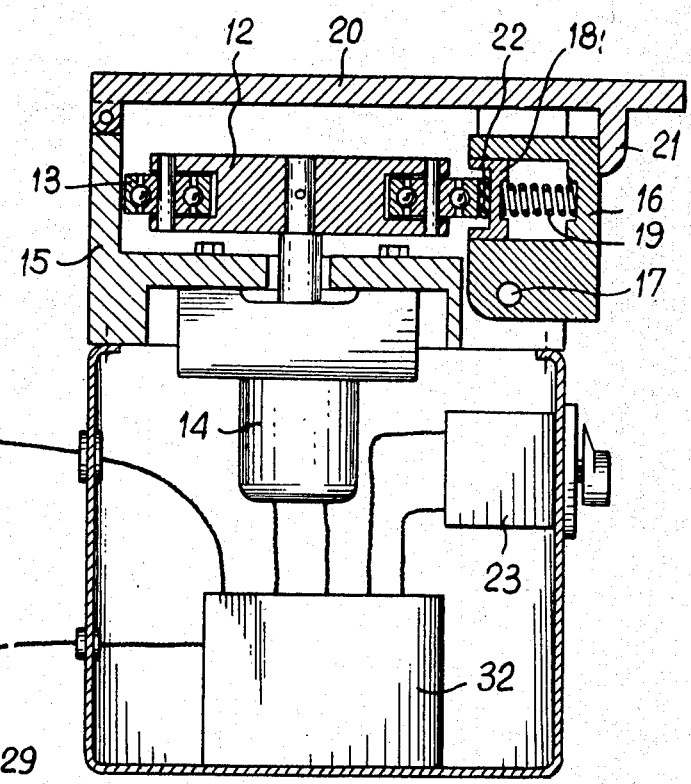
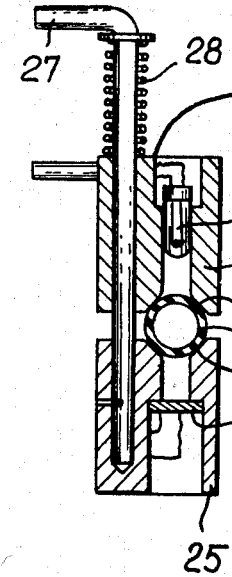
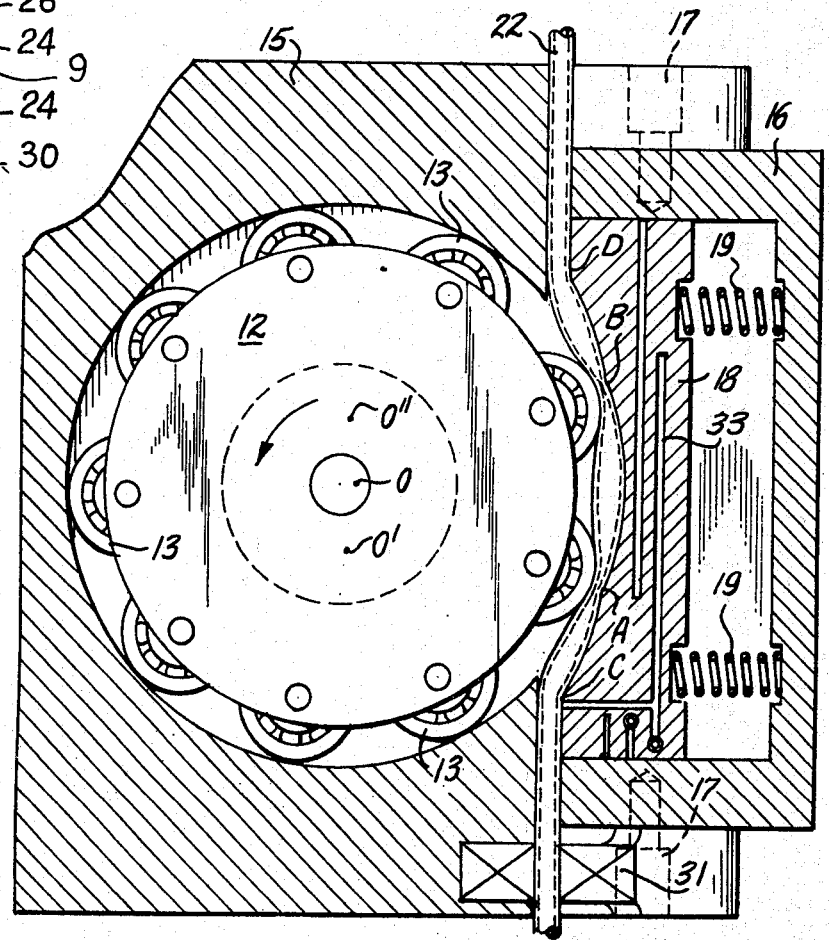
Fig.2
Fig.4
Fig.3

3,990,444

BLOOD TRANSFUSION APPARATUS

SUMMARY OF THE INVENTION

This application is a continuation-in-part of application Ser. No. 418,209, filed Nov. 21, 1973, for "Improvements in Blood Transfusion Apparatus" (now abandoned) and the filing date thereof and the priority date of its corresponding French application No. 72.42317, filed Nov. 22, 1972, is claimed for all subject matters common therewith.

This invention relates to devices which are mounted on the tube of a conventional transfusion apparatus in order to regulate and control the flow of fluid therein, drop by drop.

It should first of all be stated that a transfusion tube is ordinarily a transparent tube comprising, at a few centimeters from one of its ends, an enlarged portion known as the "drop chamber", and at its opposite end a coupling intended to receive a needle.

In the known devices, the transparent tube is partly introduced into the apparatus and is compressed by the fingers of the apparatus following a peristaltic movement. The more or less great rapidity of this movement expels more or less drops from the outlet of the needle, and this variation is produced by a motor, the speed of which is dependent on the number of drops desired and registered by the user.

This motor speed, pre-selected in dependence on the number of drops desired, cannot be accurate since it depends on the friction of the peristaltic system, and on the pressure applied on the transparent tube, and for that reason, on the voltage drops resulting on the upstream side of the motor supply circuit, even if this is previously stabilized. In order to remedy this inaccuracy, an electronic system controls the number of drops passing into the "drop chamber" and continuously compares it with the number registered or displayed, constantly correcting the motor speed through another electronic memory system.

The disadvantage of such so-called continuous correction systems is that accuracy with respect to the number displayed cannot be maintained since the speed of the motor oscillates constantly about the speed corresponding to the number displayed. Another drawback is that the transparent tube is strongly compressed by about 10 fingers placed side by side, which release it and grip it without stopping and finish in a very short time by chewing it up and damaging it.

A last disadvantage resides in the fact that in such systems the air bubbles which may be accidentally introduced into the tube cannot be detected, with all the concomitent dangers represented by these bubbles if they are injected into the circulatory system of the patient. It may also be added that the electronic complexity of such devices and also the numerous safety systems which they involve increase the cost of this apparatus to a prohibitive value for hospitals.

The device according to the invention enables these drawbacks to be avoided. In fact, in order to expel the liquid contained in the transparent tube, use is made of the compression of the said tube against a wall by means of rollers mounted on ball bearings. The rolling force thus applied only results in a very slight stress on the tube, the rollers being driven by a motor. The number of drops passing out of the end of the needle is a function of the number of impulses received by the motor, this number of impulses, displayed by the operator, being supplied by an electronic timing system. An electronic eye placed on the dropping chamber gives a stopping signal to the motor for every drop which passes, and for this reason the system thus designed provides an accurate measurement of the total flow since the periodicity of the movement of expulsion of the liquid is exactly that of one single drop per control impulse. However, it should be noted that each roller which enters or leaves the compression path modifies the rate of flow because of what is called a dead point, which corresponds to the volume of the part of the roller which compresses or releases the tube. Consequently, pumps utilizing this system effectively indicate the total output, this output varies each time a roller enters and leaves the compression path, thus transmitting a false indication to the dropping chamber. For example, when a roller enters the path no drop flows through the dropping chamber whereas in reality there is a flow downstream and thus in the vein of the patient. The converse takes place when each roller leaves the path — a drop flows through the dropping chamber, whereas there is no flow downstream.

In the case of blood perfusion the same problem of accuracy occurs but another problem exists with respect to the quality of the blood injected into the patient. It has been noted that many platelets of blood are crushed in the known devices which comprise rollers compressing the tube over a compressive path.

The present invention overcomes these disadvantages and provides a perfusion pump of high precision having no adverse effects on the quality of the product injected into the patient, particularly in the case of blood.

A detection system for air bubbles is also incorporated in the device and immediately blocks any movement of expulsion of the liquid upon the appearance of any bubble of gas.

The device forming the object of the invention comprises a wheel provided at its periphery with rollers mounted on ball bearings. This wheel rotates in a chamber having a diameter equal to twice the distance existing between the axis of the wheel and the exterior of the rollers. This construction enables all stress to be eliminated on the motor shaft, which drives the wheel directly through its centre. The chamber has an opening in its periphery, which is occupied by a movable member the inner surface of which has a radius equal to that of the chamber increased by a few tenths of a millimeter.

This movable member, biased by springs, slides in a guide which is capable of being withdrawn by rotation, so that a part of the transfusion tube may be inserted between the rotating rollers and the movable member, which compresses the tube by reason of its spring bias. The movable member must be sufficiently long for two rollers to be pressed against it at the same time, so that when the roller wheel rotates, at least one roller is always opposite the movable member in order to ensure the compression of the tube and to prevent any flow of liquid when the system stops. The surface of the movable member which contacts the tube is divided into three successive part-circular zones as hereinafter described.

The mechanical pump thus produced is accordingly characterized by:

1. A retractable guide member permitting easy introduction of the transfusion tube.

2. Partial introduction of the tube along a straight line, whereas in the known systems of this kind, it must make a complete loop on itself so as to follow closely the periphery of the bore.

3. A slidable member which compresses the tube by means of springs, thus ensuring constant fluid-tightness and the taking-up of clearances or play due to mechanical wear.

4. A surface of the slidable member which engages the tube and is divided into three successive part-circular zones, an entrance ramp, a compression zone, and an exit ramp, with the inlet and exit ramps centered on a point other than the point on which the compressive zone is centered.

The motor is driven by electrical impulses which are supplied to it by an electronic timing device. This latter is provided with a dial by means of which the user can display the number of drops which he desires to pass during a given time into the tube.

In order to complete this system, an electronic eye placed on the drop chamber gives a stopping order to the motor whenever a drop falls from the transfusion bottle into the dropping chamber. The succession of operations is therefore as follows:

emission by the electronic timing device of a signal which starts up the motor;

rotation of the roller wheel which pushes the liquid into the transfusion tube;

an electronic eye sends a stopping signal to the motor whenever a drop passes in front of its beam of light;

stopping of the system; and the compression of the tube by at least one roller preventing any further circulation of liquid awaiting a second impulse from the electronic timing device. The movement of liquid thus obtained at the dropping chamber which constitutes the visual means of control of the user, is perfectly precise since the desired display is always indicated as a number of drops per minute.

At the inlet of the transfusion tube in the mechanical pump is incorporated a detector of air bubbles which interrupts the electric supply to the motor as soon as a bubble passes into the tube. Safety systems are connected to each device. In the event of failure of any one of them, the supply of the motor is cut off and a visual and audible alarm signal is tripped. This signal will reappear at each intentional starting-up if the fault has not disappeared.

The end of the transfusion, that is to say when the bottle is empty, also prevents operation of the motor due to the fact that the electronic eye no longer detects any drops for a time longer than that fixed by the electronic time device in the case of the longest permissible time interval between two impulses.

The accompanying drawings illustrate by way of example one embodiment of the device according to the present invention.

In the drawings:

FIG. 2 is an axial sectional view through the pump proper, with the remainder of the device in side elevation with the outer casing removed;

FIG. 3 is a transverse sectional view through the pump;

FIG. 4 is a vertical sectional view through the dropping chamber; and

Figure 1:
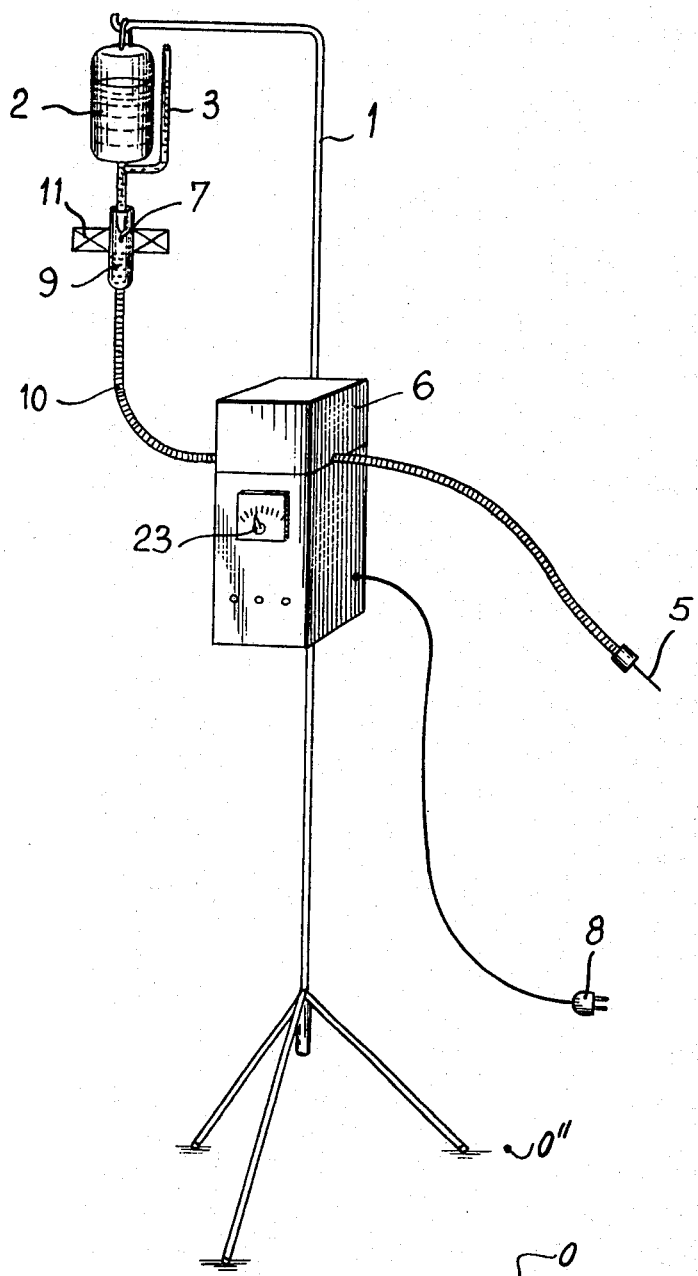
FIG. 1 is an assembly view, showing my new pump attached to perfusion tube.

FIG. 1 of these drawings represents a complete transfusion unit fixed on a support 1. It comprises a flask 2, equipped with an air-intake 3 opening into the dropping chamber 9. This chamber serves as a visual check for the passage of the drops 7 through the tube 10, which terminates at the needle 5. The pump 6 encloses the tube 10 over a small part of its length and an electronic eye 11 detects the drops, an electronic timing device 9 displaying the number of drops desired. The pump is connected to the electric supply mains by the plug 8.

As best seen in FIGS. 2 and 3 the device comprises a wheel 12 carrying rollers 13 mounted on ball bearings 13 and is mounted on the shaft of the motor 14. The rotation of the rollers takes place within a chamber defined by the casing 15, except over one portion adjacent the guide member 16. This latter may be swung by rotating it about the two pivots 17 and contains the slidable member 18, compression springs 19 being provided to urge the slidable member 18 against the bearings 13 when the guide member is in the position shown. A cover 20 holds the guide member in the illustrated (closed) position by means of the hook device 21. The transfusion tube 22 is located between the rollers 13 and the slidable member 18.

An electronic timing device 23 transmits the starting-up impulses to the motor. The electronic eye (see FIG. 4) is intended to be mounted on the dropping-chamber 9 by means of two V-members 24 reciprocally machined in two parts 25 and 26, the part 25 being fixed and the other part 26 being movable. The parts are guided by a rod 27 provided with a spring 28. The lamp 29 mounted in the part 26 directs a beam of light on the cell 30 which is mounted opposite to it. As soon as a drop passes into the beam of light, a signal is sent so as to cut off the electric supply to the motor.

A detector 31 for air bubbles is incorporated in the casing at the point where the tube enters it. Finally, a unit 32 contains the safety systems which actuate the audible and visual alarm system.

Figure 5:
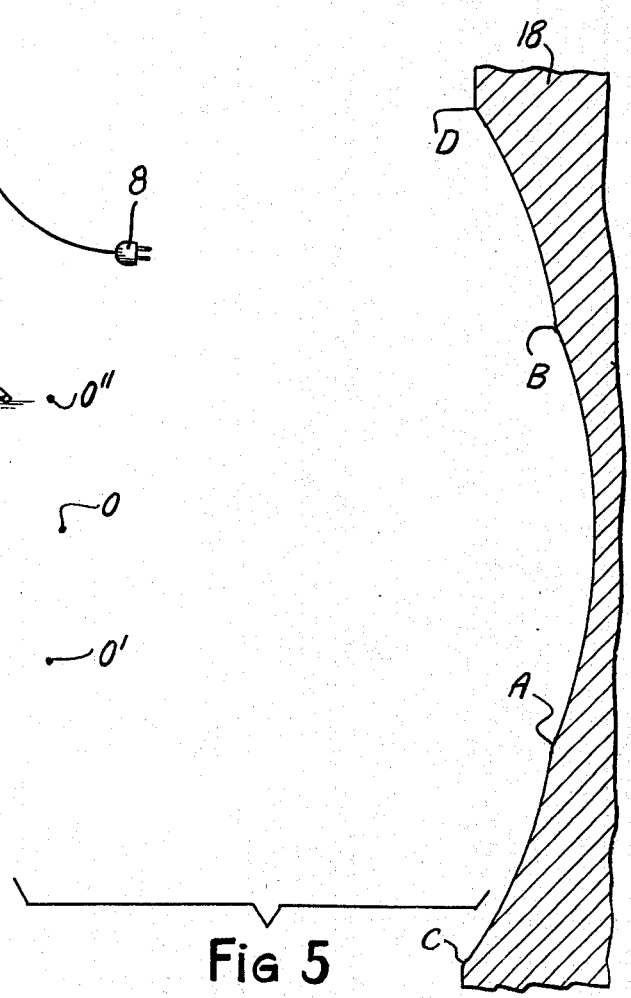
FIG. 5 is a schematic view, on a larger scale, showing the profile of the surface of the slidable member which contacts the tube.

FIG. 5 shows the profile of the surface of the slidable member which contacts the tube. It has been found that in order to overcome the disadvantages cited in connection with the present description this profile must be divided into three zones: an entrance zone AC acting as an access ramp, a compression zone AB, and a zone BD which serves as an exit ramp.

At this point certain variations are possible. However, the three zones preferably have circular profiles, the compression zone being centered on the center O of the wheel supporting the rollers, the access and exit ramps being respectively centered at O' and O''.

It is also possible to provide access and exit ramps which are symmetrical with respect to the compression zone, with the centers O' and O'' identical. FIG. 3 shows the rollers 13 compressing the tube 22 against the compression zone.

The zone AB is the effective working zone corresponding to the displacement of the liquid in the tube.

The zones AC and BD are such as to permit the roller which enters and the one which leaves (from the ramp AB) to respectively advance a constant volume on their respective ramps AC and BD as a function of their rotational advance.

In other words, the defect of other systems resulting from the entrance and the abrupt departure of the rollers from the ramp AB is eliminated due to the progressive entrance and leaving. It should be noted that when the roller G arrives at the ramp AB, the following roller H begins to compress the tube. The same effect is produced at the outlet of the ramp AB.

The advantages resulting from this system are thus, on the one hand, a greater accuracy in perfusion utilizing sterile tubes provided with dropping chambers and, on the other hand, an improvement in the quality of the product injected into the patient, especially in the case of blood. In this latter case it should be noted that the movable member should have great elasticity in all directions in order to avoid crushing certain components of the blood, such as the platelets. To this end, the movable member 18 has been provided with grooves or bores indicated by reference numeral 33 on FIG. 3.

What is claimed is:

1. Device for pumping fluid through a flexible tube at a controlled rate, which device comprises a wheel, a plurality of rollers mounted to rotate freely about equidistant points on said wheel while projecting radially from the periphery of said wheel, a casing in which said wheel is rotatably mounted, an opening in said casing positioned radially of said wheel, a pressure member slidably mounted in said opening and having a surface adjacent the periphery of said wheel, said casing, wheel and surface defining a passage for the reception of said flexible tube which traverses an arc of substantially less than 180° between said wheel and surface and leads from one side of said casing to its opposite side and through which the fluid within said tube is advanced when rotation of said wheel advances said rollers through said passage, a motor driving said wheel, a dropping chamber through which fluid in said tube flows, and means responsive to the passage of fluid drops through said dropping chamber to control the speed of said motor, said device further comprising in combination:

means resiliently biassing said pressure member toward said wheel, and
a plurality of recesses within said pressure member, which impart elasticity thereto,
said pressure member surface being divided into successive entrance, central and exit portions, each portion being substantially part-circular in section, and those ends of the entrance and exit sections which are remote from said central section begin likewise more remote from the center of curvature of said central section.

2. A device as claimed in claim 1 in which the entrance and exit sections have a common center of curvature and a larger radius of curvature than said central section.

3. A device as claimed in claim 1 in which said entrance and exit sections have the same radius of curvature as said central section, but different centers of curvature.

4. A device as claimed in claim 1 in which the length of said central section is substantially equal to the distance between the centers of successive rollers.

5. A device as claimed in claim 1 in which said slidable member is slidably mounted in a guide member which is pivotally attached to said casing so that it may be swung between a closed position in which said slidable member is urged against a tube in said passage and an open position permitting the introduction of a tube into said passage.

* * * * *